(12) United States Patent
McIntyre

(10) Patent No.: US 7,018,798 B2
(45) Date of Patent: *Mar. 28, 2006

(54) NUCLEIC ACID ANTIGENS EMBEDDED IN THERMOPLASTIC

(75) Inventor: John A. McIntyre, Indianapolis, IN (US)

(73) Assignee: Embedded Concepts, LLC, Indianapolis, IN (US)

( * ) Notice: Subject to any disclaimer, the term of this patent is extended or adjusted under 35 U.S.C. 154(b) by 481 days.

This patent is subject to a terminal disclaimer.

(21) Appl. No.: 10/355,063

(22) Filed: Jan. 31, 2003

(65) Prior Publication Data

US 2003/0134322 A1    Jul. 17, 2003

Related U.S. Application Data

(63) Continuation-in-part of application No. 09/528,181, filed on Mar. 17, 2000, now Pat. No. 6,872,576, which is a continuation of application No. 08/909,889, filed on Aug. 12, 1997, now Pat. No. 6,177,282.

(51) Int. Cl.
    *C12Q 1/68*    (2006.01)

(52) U.S. Cl. .......................... 435/6; 435/7.1; 536/23.1

(58) Field of Classification Search .................... None
    See application file for complete search history.

(56) References Cited

U.S. PATENT DOCUMENTS 6,177,282 B1 * 1/2001 McIntyre .................... 436/518
6,872,576 B1 * 3/2005 McIntyre .................... 436/518

FOREIGN PATENT DOCUMENTS

WO    WO 95/01998    1/1995
WO    WO 99/08113    2/1999

* cited by examiner

*Primary Examiner*—James Martinell
(74) *Attorney, Agent, or Firm*—Antonelli, Terry, Stout and Kraus, LLP.

(57) ABSTRACT

An assay device is made by combining a polynucleic acid with a molten material capable of solidifying into a solid thermoplastic or thermosetting material and then allowing the molten material to solidify. The thus-formed thermoplastic solid material has at least some molecules of the polynucleic acid exposed on the surface of the thermoplastic solid material in an orientation wherein the polynucleic acid is bindable to a binding partner by specific binding. The invention further relates to a solid phase substrate having a polynucleic acid embedded therein. The invention further relates to the use of a solid phase substrate having a polynucleic acid embedded therein for hybridization assays and immunoassays to detect anti-nucleic acid antibodies.

24 Claims, 3 Drawing Sheets

NUCLEIC ACID ANTIGENS EMBEDDED IN THERMOPLASTIC

CROSS REFERENCE TO RELATED APPLICATIONS

The present application is a Continuation-in-part of U.S. patent application Ser. No. 09/528,181, filed Mar. 17, 2000 now U.S. Pat. No. 6,872,576, which application is a continuation of U.S. patent application Ser. No. 08/909,889, filed Aug. 12, 1997, now U.S. Pat. No. 6,177,282. The disclosures of each of these applications are incorporated herein by reference.

FIELD OF THE INVENTION

The present invention relates to the preparation of immobilized antigen comprising ribonucleic and/or nucleic acids and the use of the immobilized antigen in immunoassays as well and other biomedical applications.

BACKGROUND TO THE INVENTION

Immunoassays have been used for decades as a means to assay for the qualitative and quantitative presence of antigens or antibodies in a sample. Immunoassays have many practical uses, including the diagnosis of certain diseases by detecting antigens that are characteristic of the disease and the screening of blood or other fluids by detecting harmful substances or organisms, or antibodies associated with the presence of the harmful substances or organisms. For example, screening of blood or other fluids for autoantibodies to DNA can be used in the diagnosis of autoimmune diseases.

One of the most common immunoassay techniques uses a solid phase matrix to which either an antigen or antibody is bound. For example, typical ELISA systems use plastic (polystyrene) 96-well plates (Microtiter plates) that have been adapted and/or modified to provide optimal binding of the antigenic substance or antibodies.

Various methods are known for attaching molecules to surfaces such as ELISA plates. These methods include attaching the molecules to the surface of derivatized surfaces by covalent binding or coating surfaces with molecules dissolved in a solvent so that the molecules adhere to the surface when the solvent evaporates.

These methods have various disadvantages relating to reproducibility, sensitivity and quantification. In a solid phase immunoassay, it is important that the attached antigen or antibody be present on the surface in an orientation so that the specific portion of the molecule that participates in ligand/receptor binding is exposed and so that the binding site is not altered or distorted. In other words, it is important that the features that make a particular molecule useful in an immunoassay not be destroyed in the process of attaching the molecule to a surface. Moreover, to insure reproducibility, the attached antigen or antibody should resistant to damage, alteration or removal during the typical harsh conditions of an immunoassay.

When molecules are attached to a derivatized surface by covalent binding, there is likelihood that chemical reactions occurring during the binding event will also alter the receptor/ligand-binding site. Furthermore, the molecules might be attached to the surface in an orientation such that the specific receptor/ligand-binding sites are not accessible. This reduces the sensitivity of the immunoassay.

When a molecule is attached to a surface by methods of coating and solvent evaporation, there is a difficulty in assuring that the molecules are bound to the surface in a reproducible manner. Moreover, if an antigen or antibody is coated onto a surface of untreated plastic, which tends to be hydrophobic, the antigen or antibody may, depending on the particular solute and surface being used, orient itself so that the hydrophobic portion of the antigen or antibody adheres to the hydrophobic plastic surface. There is then a likelihood that the receptor/ligand binding portion of the antigen or antibody will be obscured, resulting in reduced sensitivity.

A further problem with typical methods of attaching antigens and antibodies to pre-formed surfaces is that these methods tend to be expensive and labor intensive.

ELISA-based testing for autoantibodies to DNA is typically performed to assess for autoimmunity. A generic name for this type of testing is "ANA", which stands for anti-nuclear-antibodies. The present invention demonstrates that autoantibodies to DNA embedded in polystyrene are easily detectable in patients with known ANA positive activity. The benefits of using embedded DNA are manifold and have advantages over the traditional methods of ELISA-based ANA testing. First, the embedded DNA will not fall off the plastic as it may when using the conventional "coating" of plastic which relies on non-specific (electrostatic) adherence to the ELISA plate wells. Thus, there can be standard concentrations of DNA embedded into the plastic and this will not change regardless of who performs the test and where the testing is preformed. Second, the embedded DNA antigens will have an indefinite shelf life. Third, by mixing the DNA with the plastic stock, there is no need for the expensive technician time that is required to "coat" the plate wells. Fourth, if desirable, the DNA embedded wells can be recycled by adding low pH to remove the bound antibody. To quantify the level of antibody in blood, one must have a reproducible standard assay since there is a correlation between the number of antigen molecules on the solid support and the number of bound antibody molecules resulting from sample application.

In another aspect of the present invention, a polynucleic acid with a specific sequence may be embedded into a solid material for use in a hybridization assay to detect complementary strands of polynucleic acid, such as viral or bacterial DNA or RNA. The use of embedded DNA for this purpose has the same advantages over conventional hybridization assays as it does in immunoassays, including greater reliability, improved shelf life, lower cost of manufacture and reusability.

SUMMARY OF THE INVENTION

It is an object of the present invention to provide a standard and stable preparation of a solid material having polynucleic and/or polyribonucleic acid exposed to the surface in an orientation useful for participating in hybridization assays or immunoassays, wherein the solid material is produced by a method that is easily reproduced on a large scale, without relying on careful use by an operator.

It is a further object of the present invention to provide a thermoplastic or thermosetting solid material having a polynucleic acid evenly throughout the solid material so that the distribution of polynucleic acid on the surface of the particles is of a predefined quantity.

It is a further object of the present invention to provide a thermoplastic or thermosetting solid material having a binding agent evenly throughout the solid material so that the polynucleic acid will not leach or elute from solid phase particles.

It is a further object of the present invention to provide a thermoplastic or thermosetting solid material having a polynucleic acid evenly throughout the solid material wherein, after the material is used in a hybridization assay or immunoassay, the bound binding partner may be stripped off and the particles reused for the same or other purposes.

It is a further object of the present invention to provide a thermoplastic or thermosetting solid material having a polynucleic acid evenly distributed throughout the solid material for an immunoassay involving the binding of an antipolynucleic acid antibody to the polynucleic acid.

It is a further object of the present invention to provide a thermoplastic or thermosetting solid material having a polynucleic acid evenly distributed throughout the solid material for a hybridization assay involving the binding of a complementary strand of a polynucleic acid to the immobilized polynucleic acid.

These and other objects are attained by providing a polynucleic acid-containing monolithic thermoplastic or thermosetting solid material, wherein molecules of the polynucleic acid are evenly and unreleasably dispersed throughout the material, wherein the molecules of the polynucleic acid are not chemically coupled to the solid material, wherein at least some of the molecules of the polynucleic acid are exposed to the surface of the solid material in an orientation wherein the polynucleic acid is bindable to a binding partner (such as a complementary strand of polynucleic acid or an antibody to polynucleic acid) by specific binding. The polynucleic acid-containing material is made by mixing the polynucleic acid with a fluid material that is to become the solid material so that the polynucleic acid becomes evenly distributed within the fluid material to form a mixture, adding the mixture to a mold, and allowing the mixture to solidify so that the mixture is formed into a solid material having molecules of the polynucleic acid evenly distributed throughout the material and exposed to the surface of the material. After it is formed, the solid material is released from the mold.

The polynucleic acid-containing solid material as described above may be used in any conventional immunoassay or hybridization assay format requiring a material with a polynucleic acid immobilized thereon.

In the present invention, the problems associated with prior art methods for attaching polynucleic acid to a surface are avoided. Because the molecules of the polynucleic acid are not covalently bound to the surface of the material and are not otherwise involved in chemical reactions (such as polymerization) during an attachment process, there is less danger of loss of antigenic or hybridization binding sites because of chemical reactions. Because the molecules of the polynucleic acid are embedded into the material and not just coated onto the surface of the material, there is less danger of removal or loss of the antibodies or antigens and stability of the polynucleic acid on the surface of the material is maintained over time. The present invention avoids the coating step that resulted in variations in coating, instability on the surface and inconsistent results.

In one aspect, the present invention relates to mixing a polynucleic acid with a thermoplastic material heated to a molten state. The mixture is then used in conventional injection and blow molding to form the solid phase. The process provides for an even distribution and constant concentration of the polynucleic acid in the plastic material.

In another aspect, the present invention relates to mixing a polynucleic acid with monomers that can polymerize in the presence of heat and/or polymerization catalysts or crosslinking agents and then allowing polymerization to take place to form a solid material. This process also provides for an even distribution and constant concentration of the polynucleic acid in the plastic material.

The figures are drawn to illustrate certain features of the invention and are not drawn to scale with respect to other components. Furthermore, certain components are drawn schematically when numerous different designs and assay formats are possible while practicing the invention.

DESCRIPTION OF THE PREFERRED EMBODIMENT

One embodiment of the present invention relates to the incorporation of polynucleic acid into solid phase substrates, particularly plastic materials, the products produced thereby (such as tubes, beads and multi-well plates), and binding assays using these products. While some specified examples involve an ELISA, the present invention is not limited to any particular immunoassay or hybridization format.

Figure 1:
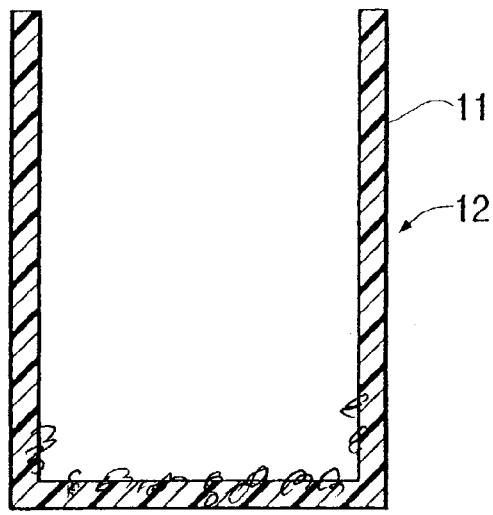
FIG. 1 is a sectional view of a test tube made of a thermoplastic solid material with molecules of polynucleic acid dispersed throughout it.
Figure 2:
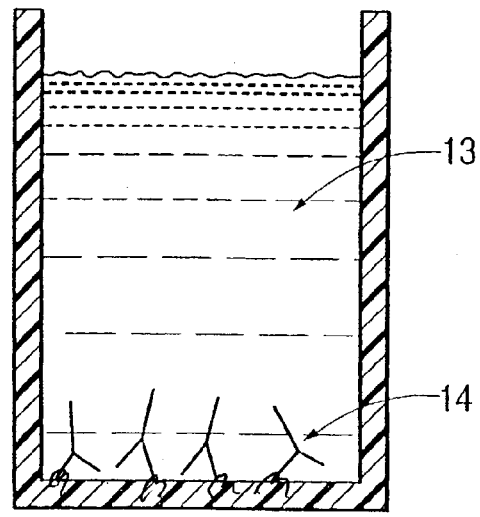
FIG. 2 is the same test tube after a sample liquid containing a binding partner is added and allowed sufficient time for the binding partner to bind to the polynucleic acid.

The polynucleic acid is incorporated into a plastic material to prepare a solid-phase-embedded polynucleic acid for use in an assay. In the solid phase substrate 12, the polynucleic acid 11 is uniformly distributed throughout and embedded in the solid phase substrate 12. The solid phase substrate 12 may be in the form of a container, such as a well. A liquid sample 13 containing a binding partner 14 is added to the container and the binding partner binds to the binding agent. As depicted in FIG. 2, the binding partner may be an antibody molecule, which has been enlarged for easy visualization. The liquid sample is then decanted or aspirated and washed. A labeling agent 15 that binds to the binding partner 14 is then added to the container. The container is again decanted or aspirated and washed to remove any unbound labeling agent. The label 16 is then detected in a manner appropriate for the particular label. When using a fluorescent label, the presence of the label may be directly observed by exposing it to appropriate wavelengths of light and observing the emission of other wavelengths corresponding to the fluorescent label. The label may be detected qualitatively or measured quantitatively and either bound to the solid phase substrate or in the removed liquid containing the unbound labeling agent. (In the drawings, the polynucleic acid, binding partner and labeling agent are not drawn to scale.)

As used herein, the term "polynucleic acid" refers to any single or double stranded DNA or RNA, from natural sources or artificially synthesized. The strands of the polynucleic acid should be long enough so that the polynucleic acid is useful for hybridization assays or immunoassays, and long enough so that one or both ends of the strands of can become entrapped in the solid material as it hardens. For some purposes, oligonucleotides of two or more nucleic acid bases may be sufficient. The particular polynucleic acid is selected according to the particular intended use of the solid material. For example, if the solid material is to be used in an immunoassay to search generally for the presence of DNA-binding antibodies in the serum of a patient, the polynucleic acid could be a crude preparation of genomic DNA. For hybridization assays, specific sequences that are complementary to a target DNA or RNA would be used as the polynucleic acid.

The term "binding partner" refers to a component that is free in a liquid and binds to the previously embedded polynucleic acid to become insolubilized. For example, the binding partner may be an antibody to the polynucleic acid or a complementary stand of polynucleic acid that hybridizes to the immobilized polynucleic acid.

Examples of suitable materials for the solid material include thermoplastic polymers such as polystyrene, polyethylene, polypropylene, polycarbonate, polyethylene terephthalate, polyester (e.g. Dacron), polyurethane, polyolefin, polyvinyl alcohol, PVP, methyl methacrylate and other polymers used in contact with tissues or biological fluids.

Other plastic materials such as thermosetting polymers may be used. In such a situation, the polynucleic acid is mixed with the monomers or oligomers, which are then heated to polymerize or cross-link the composition, thereby entrapping the polynucleic acid. The plastic substrate may also be made by chemical, ultraviolet light or other non-thermal polymerization methods as well. A variety of hardeners, clarifiers, and plasticizers may be added to give the substrate its desired physical properties. In such a situation, the polynucleic acid may be mixed with a substrate forming material (e.g. monomers) prior to or simultaneous with the addition of the hardening agent or the polymerization agent. Examples include epoxies and some of the same polymers listed above under thermoplastic polymers.

The material forming the solid material may be carefully chosen or modified to accommodate the temperature and chemical limitations of polynucleic acids. For example, certain polystyrenes become molten at a relatively low temperature. These temperatures are compatible with binding agents made of polynucleotides, many proteins, lipids and most organic compounds. Indeed, certain polystyrenes become molten at temperatures only twice as hot as those used in the preparation of antigens prior to running them in a polyacrylamide gel, particularly the heat-denaturing step. The temperature at which thermoplastic polystyrene becomes molten may be further lowered by the addition of various chemicals. The modification of the physical and optical properties of plastic materials is known per se. The amount of polynucleic acid present in the solid phase may vary widely; for example, from about 0.00000001 to about 500 weight parts per 1000 weight parts of material forming the solid phase. Typically, the weight amount of polynucleic acid that is added is trivially small compared to the weight amount of plastic and therefore is unlikely to significantly affect its properties. The same can be said for using other materials.

Preferably, the solid material is a monolithic solid material, meaning that it is a discrete solid in which molecules of the polynucleic acid are be embedded and having a surface on which portions of molecules of the polynucleic acid can be exposed. In other words, the solid material is not a non-hardened material such as a gel, wax or membrane. The monolithic solid material may be in the form of particles of sufficient size to have polynucleic acids embedded therein.

Figure 4:
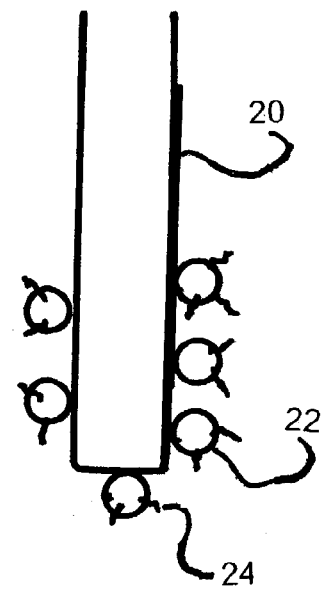
FIG. 4 is a sectional view of a substrate having attached particles of a thermoplastic solid material having molecules of polynucleic acid dispersed throughout it.

The thermoplastic or thermosetting solid material that constitutes the solid material with embedded DNA may be molded into any form, such as particles, beads, tubes, flasks, multi-well plates, etc. Further, the solid material with embedded DNA may be subjected to cutting, grinding or other mechanical processes to expose a greater amount of surface area. Ground particles of solid material with embedded DNA may then be attached to an inert solid substrate or carrier by, for example, gluing or other means. For example, as shown in FIG. 4, a solid carrier 20 with attached thermoplastic solid particles 22 with embedded DNA 24 may be in a form such as a rod or stick or other oblong object that can be easily handled and that can be inserted into a sample solution.

An entire object, such as an ELISA plate, need not be made of the solid phase composition of the present invention; rather, only the solid phase portion in contact with the liquid sample needs to be made of such a material. For example, wells or a strip of wells of a multi-well plate may be made of the composition of the present invention whereas the balance of the multi-well plate may be made of any conventional plastic or even metal. This arrangement permits one to remove an individual well for further analysis. Also, since the composition of the present invention is more expensive than the solid phase material without the polynucleic acid, beneficial economies result from using the combination to make certain parts that are contacted with the liquid containing the sample.

The physical steps involved in creating the solid material of the present invention include mixing the polynucleic acid with a material that is to become the solid phase or substrate. When the material is a thermoplastic, the polynucleic acid to be embedded may be mixed with a small plastic pellet stock and heated until molten or the polynucleic acid may be mixed with the molten plastic itself. Uniformity in mixing the polynucleic acid and the plastic pellets may be enhanced by solubilizing the nucleic acids in hot water, mixing with the pellets and allowing the water to evaporate. Lyophilizing the DNA/polystyrene mixture can accelerate evaporation. This ensures a more even distribution on the plastic pellets and a consistent distribution throughout the mixture. The molten plastic is then formed into a plastic receptacle of any desired shape. The polynucleic acid is distributed evenly throughout the plastic receptacle. Typically, no chemical reaction occurs between the plastic substrate and the polynucleic acid, nor is a chemical reaction particularly desirable. The individual molecules of the polynucleic acid are held in the plastic substrate because the plastic material solidifies around enough of the molecule to hold it in place. (Any polynucleic acid molecule is not held in place would simply be washed away as excess.) The reason why the solid material with embedded polynucleic acid is useful for immunoassays and hybridization assays is that out of all of the molecules of polynucleic acid that are mixed and randomly distributed throughout the plastic material, at least some of them will be exposed to the surface of the material, and at least some of the molecules exposed on the surface will be in an orientation that is useful for binding assays. Once the solid material is solidified, the amount of polynucleic acid that is exposed on the surface in a useful orientation is fixed. The solid material can be tested to determine the amount of polynucleic acid that is fixed on the surface in a useful orientation and calibrated.

Figure 3:
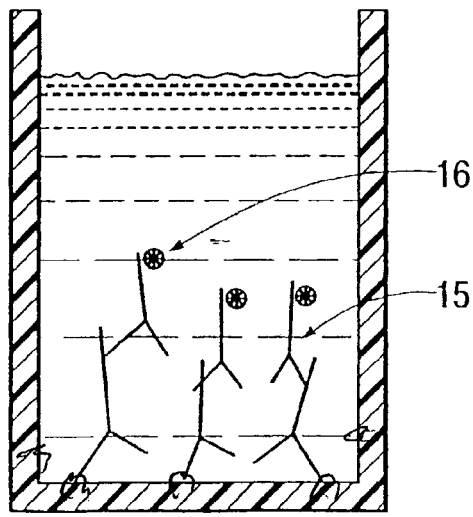
FIG. 3 is the same test tube as FIG. 2 after washing and adding a labeling agent (labeled antibody or protein G) that binds to the binding partner insolubilized on the test tube.

Any of the conventional binding assay formats may be used provided that the polynucleic acid is first embedded in a solid phase before adding a binding partner. The patent literature is replete with dozens of different binding formats in the immunoassay, nucleic acid hybridization assay and biospecific binding assay arts. Common binding formats include sandwich assays, which are shown in FIGS. 2–3. Competitive binding assays may be used where a second binding partner, is added before, during or after adding the binding partner so that they compete for binding to the polynucleic acid. Alternatively, a labeling agent may be used to bind to the binding partner in competition with the polynucleic acid. Typically, either the binding partner or the second binding partner is labeled directly or indirectly by a labeling agent for easy detection of bound or free label.

As used herein, the term "sample" refers to any composition from any source that contains a binding partner or that is to be tested for the presence of a binding partner. The binding partner is typically solubilized in a fluid before use in a binding assay according to the present invention. The sample is preferably a biological sample, more preferably a biological fluid.

For many binding assay formats, a labeling agent is needed in addition to the polynucleic acid and the binding partner to determine whether the polynucleic acid and the binding partner actually bind to each other. The labeling agent is typically a conjugated chemical compound that has two properties. First, the labeling agent must contain a label; second, the labeling agent must physically or chemically bind to the binding partner or the polynucleic acid. Typically, these two properties belong to different portions of the labeling agent wherein the two portions are chemically coupled together.

Examples of suitable labels include: a radioactive moiety, an enzyme or portion thereof, an enzyme substrate, a fluorescent moiety, a chemiluminescent moiety, a quencher, a moiety which reflects or adsorbs light or other electromagnetic radiation, a magnetic, paramagnetic or supermagnetic particle, a chemical detectable by magnetic resonance, a solid or porous particle or sheet or any moiety which is readily detectable directly or which interacts with another substance (such as another chemical moiety, a polymerization initiator, etc.) to result in a detectable change.

Examples of the portion of the labeling agent which binds to the binding partner include: an antibody, an antigen, a hapten, protein A or G, DNA, an adsorbent of the binding partner or binding agent, biotin, avidin/strepavidin, and moieties which chemically react with the binding partner or binding agent.

The detecting agent may be in plural portions such as a rabbit anti-mouse IgG antibody labeled with the enzyme glucose oxidase and separately free in another solution, the enzyme substrate glucose, a second enzyme peroxidase and 3,3',5,5' tetramethylbenzidine as a chromogen.

The polynucleic acid-containing solid material of the present invention has a distinct advantage over conventional materials having insolubilized components for conventional binding assays. Embedding the polynucleic acid in a solid material in accordance with the present invention permits one to expose the polynucleic acid to otherwise unacceptable chemical and/or physical conditions. For example, when conducting an ELISA assay, the blocking step can be omitted and instead, a detergent such as 0.05% Tween can be added to the buffer. When the assay is complete, one may strip bound binding partner using dilute acid, chaotropic agents, denaturing or other rather harsh techniques that could not be used if the polynucleic acid were merely adsorbed to the solid material. This permits one to reuse the same solid material, which saves the time and effort of preparing and calibrating a new solid material.

Moreover, the fact that a binding partner may be stripped from an embedded binding agent such as a polynucleic acid without harming the solid material having the embedded binding agent allows the use of the material of the present invention to determine the strength of binding affinity or hybridization. For example, after measuring the presence of a binding partner in an initial step, the binding partner may be partially stripped, starting with a weak chaotropic agent and continuing with progressively stronger chaotropic agents, while measuring the extent of binding remaining after each step. This technique could be useful in diagnosing ANA. Even normal individuals have some small level of anti-DNA antibodies, but it has been discovered in some instances (results not shown) that the antibodies produced by ANA patients bind more tightly to DNA than the antibodies produced by normal individuals. Thus, the strength of binding of an individual's anti-DNA antibodies to DNA could be measured by the above technique.

Having described the invention, the following examples are given to illustrate specific applications of the invention, including the best mode now known to perform the invention. These specific examples are not intended to limit the scope of the invention described in this application.

EXAMPLE 1

One kilogram of polystyrene stock pellets are mixed with 50 ng lyophilized oligonucleotide with a poly-T tail having an average length of greater than about 1.0 kb by a steel rod in a stainless steel bowl to thoroughly distribute the oligonucleotide throughout the polystyrene pellets. The mixture is extruded in a heated auger that melts the polystyrene and injects the mixture into a mold for 15 cc conical tubes.

The molten material is solidified by cooling. The finished conical tube is then removed from the mold and is ready for immediate use without the addition of any polynucleotide coating.

EXAMPLE 2

The tubes produced in Example 1 are then filled with a hybridization buffer containing 0.5 ng of sample DNA having an average length of about 600 bp and a sequence complementary to the oligonucleotide embedded in the plastic. The sample DNA has incorporated digoxigenen on approximately 10% of the TTP's in the sample DNA sequence. Control tubes omit addition of the sample DNA. The tubes are placed in a boiling water bath until the temperature of the hybridization buffer remains above 900° C. for two minutes. The tubes are removed and allowed to cool to the optimal hybridization temperature for the oligonucleotide and remain at that temperature for 60 minutes. The liquid is decanted from the tubes and they are washed with a series of high salt buffers. The tubes are blocked with 10% bovine serum albumin, a blocking agent, for 30 minutes at room temperature. After the blocking agent is decanted, buffer containing alkaline phosphatase labeled antibody to digoxigenen is added and incubated at room temperature for 60 minutes. The tubes are washed 3 times with a saline buffer. Paranitro-phenylphosphate in diethanolamine buffer is added and the tubes are incubated in the dark for 60 minutes. The amount of color development is determined spectrophotometrically and compared to control tubes in which no sample DNA is added to determine the presence of alkaline phosphatase indicating the tubes with incorporated DNA effectively serve as a solid phase for a DNA binding assay.

EXAMPLE 3

Calf thymus DNA (1 gram) was obtained from ICN Biomedicals (cat. No. 195129). The DNA was solubilized in 200 ml of purified water. To facilitate getting the DNA in solution, the DNA-water mixture was placed into a 70° C. water bath overnight. After monitoring to ensure that the DNA was in solution, the DNA-water mixture was added to 228 gm of medical grade polystyrene, which had been pulverized in a Braun coffee grinder. The slurry that was formed was stirred until well mixed, then poured onto a sheet of foil for placement into a freeze dryer. The lyophilized DNA polystyrene mixture was placed into a 500 ml beaker and stirred until the polystyrene powder resembled the product of the coffee grinder. These steps were performed to provide equal distribution of the DNA in the polystyrene.

Figure 5A:
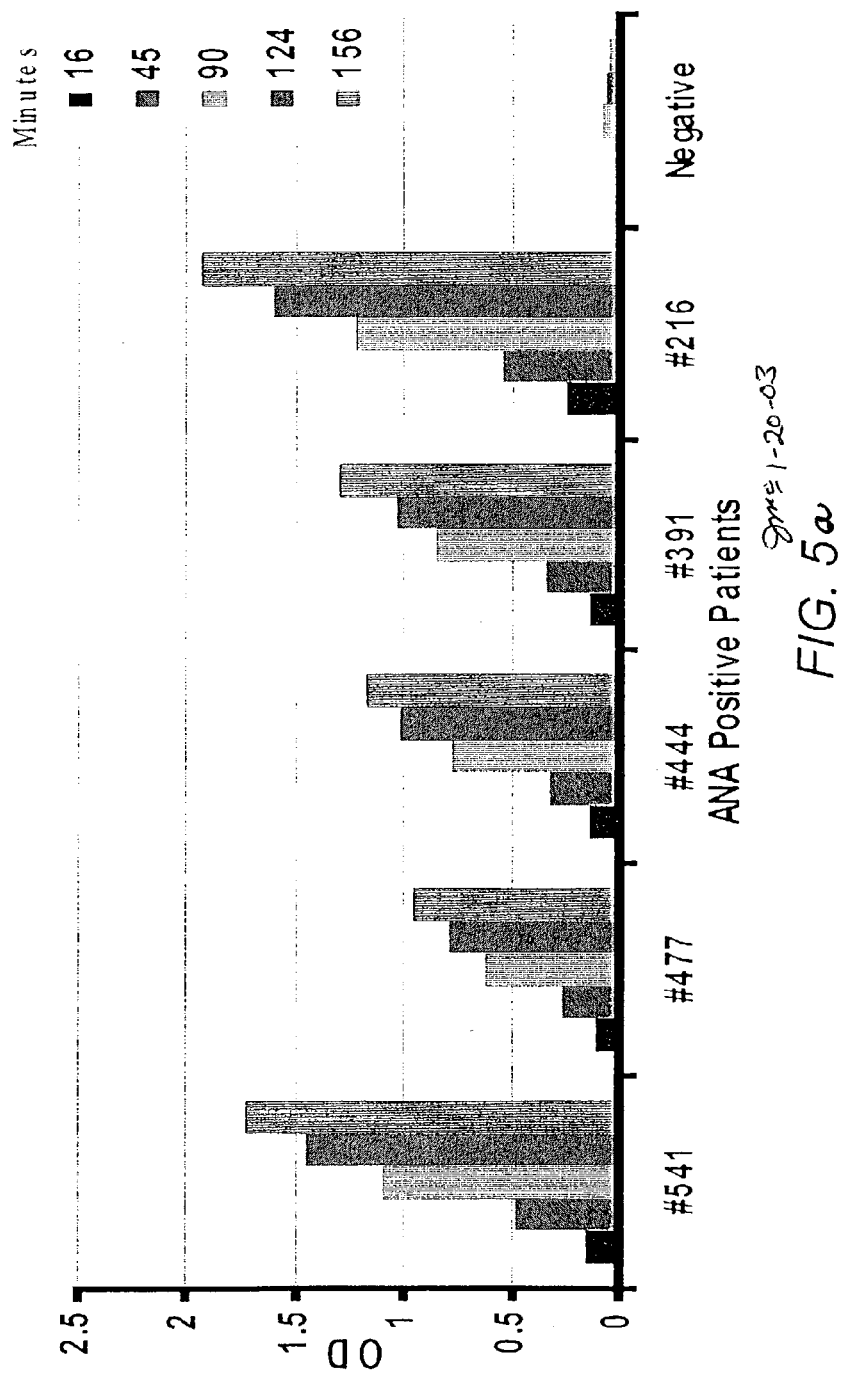
FIG. 5a is a histogram showing the results of ELISA testing of 5 known ANA positive patents and 1 negative control.

The DNA polystyrene mixture was injection molded into the shape of receptacles or wells suitable for performing an ELISA. To perform an ELISA using the DNA-embedded polystyrene wells, the wells were blocked for 1 hour with 5% BSA in Tris buffer. After washing, patient sera diluted 1/20 in 1% BSA buffer was added to the wells and incubated for 1 hour. Additional washes were followed by incubation in an alkaline phosphatase labeled antihuman IgG and substrate development was allowed to proceed. FIG. 5a depicts the results of ELISA testing of 5 known ANA positive patients (designated by patent #s) and 1 negative control individual. Non-specific background (wells with no human sera) was subtracted from the positive ELISA values. FIG. 5a demonstrates that anti-DNA antibodies can be detected by this ELISA method in ANA positive patients.

EXAMPLE 4

Figure 5B:
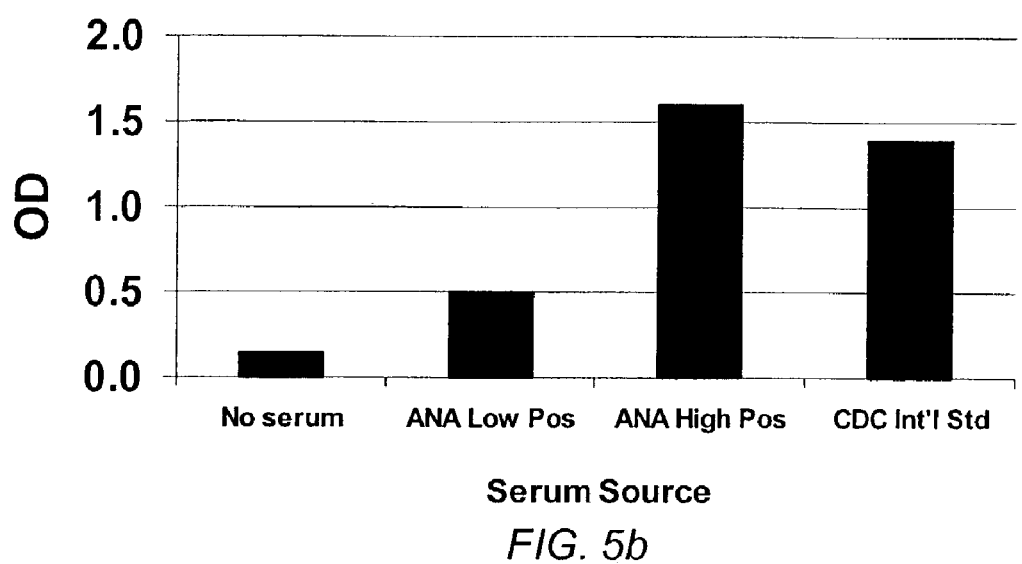
FIG. 5b is a histogram showing low and high positive ANA serum samples compared to an International Standard ANA serum obtained from the Centers for Disease Control. Data in FIG. 5a were obtained by using a "Dip-Stick" methodology (see FIG. 4), which consisted of ground DNA-embedded polystyrene, attached by glue to the distal end of a plastic straw.

A solid polystyrene material having embedded DNA was ground into particles. The particles were then glued with super glue onto the distal end of a plastic coffee stirring stick, thereby forming a "dipstick" having the particles of the DNA embedded material attached thereto. The dipstick was then used in an anti-DNA antibody detection assay in a manner similar to Example 3, except using the dipstick to perform the assay instead of a receptacle made of the DNA-embedded material. FIG. 5b demonstrates that the embedded DNA can be used to detect anti-DNA antibodies in this modified DipStick example. This method may be useful for the development of point of care testing.

The foregoing description of the specific embodiments reveal the general nature of the invention so that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

What is claimed is:

1. A composition comprising a thermoplastic or thermosetting solid material having molecules of a polynucleic acid evenly dispersed throughout the solid material, wherein the polynucleic acid is not chemically coupled to the solid material and wherein the polynucleic is held in the solid material so that the polynucleic acid does not leach or elute from the solid material, wherein at least a fraction of the molecules of the polynucleic acid is exposed to a surface of the solid material in an orientation wherein the polynucleic acid is bindable to a binding partner by specific binding.

2. The composition according to claim 1 wherein the thermoplastic or thermosetting solid material is in a form of a bead, plate, tube or well.

3. The composition according to claim 1 wherein the composition is a component of an immunoassay device.

4. The composition according to claim 1 wherein the composition is a component of a hybridization assay device.

5. A composition comprising a thermoplastic or thermosetting solid material having molecules of a polynucleic acid evenly dispersed throughout the solid material, wherein the polynucleic acid is not chemically coupled to the solid material and wherein the binding agent is held in the solid material so that the polynucleic acid does not leach or elute from the solid material, wherein at least a fraction of the molecules of the polynucleic acid is exposed to a surface of the solid material in an orientation wherein the polynucleic acid is bindable to a binding partner by specific binding, wherein the solid material having the polynucleic acid evenly dispersed throughout is formed by a process comprising the steps of:

mixing the polynucleic acid with a fluid material that is to become the solid material so that the binding agent becomes evenly distributed within the fluid and solid material to form a mixture, forming the mixture into a specific shape and allowing the mixture to solidify to form a solid material having the specific shape and wherein the polynucleic acid is not a participant in a reaction of solidifying the mixture.

6. The composition of claim 5 wherein the solid material having the specific shape is ground into particles.

7. The composition of claim 6 wherein the particles are attached to a solid carrier.

8. The composition of claim 7 wherein the solid carrier has a shape such that it can be immersed in a sample solution.

9. A method for preparing a thermoplastic or thermosetting solid material having molecules of a polynucleic acid evenly dispersed throughout the solid material, wherein the polynucleic acid is not chemically coupled to the solid material and wherein the binding agent is held in the solid material so that the polynucleic acid does not leach or elute from the solid material, wherein at least a fraction of the molecules of the polynucleic acid is exposed to a surface of the solid material in an orientation wherein the polynucleic acid is bindable to a binding partner by specific binding, the method comprising the steps of:

mixing the polynucleic acid with a fluid material that is to become the solid material so that the polynucleic acid becomes evenly distributed within the fluid material to form a mixture, forming the mixture into a specific shape and allowing the mixture to solidify to form a solid material having the specific shape and wherein the polynucleic acid is not a participant in a reaction of solidifying the mixture and wherein because of random motion of the molecules of the polynucleic acid during the step of mixing, at least a fraction of the molecules of the polynucleic acid are exposed to a surface of the solid material in an orientation wherein the polynucleic acid is bindable to a binding partner by specific binding.

10. The method of claim 9 wherein the fluid material comprises a thermoplastic molten material that forms the thermoplastic solid material when cooled.

11. The method according to claim 9 wherein the fluid material contains a monomer or oligomer that forms a thermosetting solid material when polymerized or crosslinked.

12. The method according to claim 11 wherein the monomer or oligomer is polymerized or crosslinked by heat or the addition of a crosslinker.

13. The method of claim 9 comprising the further step of grinding the solid material having the specific shape into particles.

14. The method of claim 13 comprising the further step of attaching the particles to a solid carrier.

15. The method of claim 14 wherein the solid carrier has a shape such that it can be immersed in a sample solution.

16. A binding assay method for detecting the presence of a binding partner, the method comprising the steps of:
providing a composition comprising a thermoplastic or thermosetting solid material having molecules of a polynucleic acid evenly dispersed throughout the solid material, wherein the polynucleic acid is not chemically coupled to the solid material and wherein the polynucleic is held in the solid material so that the polynucleic acid does not leach or elute from the solid material, wherein at least a fraction of the molecules of the polynucleic acid is exposed to a surface of the solid material in an orientation wherein the polynucleic acid is bindable to a binding partner by specific binding,
contacting a sample suspected of containing the binding partner with the composition for a sufficient time and under sufficient conditions to permit molecules of the binding partner, if present, to bind to molecules of the polynucleic acid exposed on the surface of the solid material, and
detecting the presence or absence of binding of the binding partner to the polynucleic acid.

17. The binding assay method according to claim 16, further comprising contacting a labeling agent with the binding partner or the polynucleic acid before or after said binding partner binds to the polynucleic acid.

18. The binding assay method according to claim 17, wherein said binding assay method is an immunoassay and the binding partner is an immunoglobulin or immunoglobulin fragment that binds to polynucleic acids.

19. The binding assay method according to claim 17, wherein the assay method is performed for the detection of antibodies to nucleic acids associated with an autoimmune disease.

20. The binding assay method according to claim 17, wherein said binding assay method is a hybridization assay and the binding partner is a target polynucleic acid that hybridizes to the polynucleic acid in the thermoplastic solid material.

21. The binding assay method according to claim 17, wherein said solid material comprises at least part of a container designed to hold the sample.

22. The binding assay method of claim 17 including the further step of regenerating the solid material by removing the binding partner after the step of detecting the binding partner, wherein the step of removing the binding partner is carried out by adding a reagent or changing physical conditions so as to break any bonding between the binding partner and the polynucleic acid of the solid material and stripping the binding partner free from thermoplastic solid material.

23. The method according to claim 22, wherein the binding partner is stripped by acid, salt or chaotropic agent.

24. The method of claim 23 wherein the removal of the binding partner is carried out in successive steps starting with a weak chaotropic agent and continuing with progressively stronger chaotropic agents, while measuring the extent of binding remaining after each step, so that the binding affinity of the binding partner can be measured.

* * * * *